United States Patent [19]

Holcombe, Jr. et al.

[11] 3,948,813

[45] Apr. 6, 1976

[54] OXYGEN SENSITIVE, REFRACTORY OXIDE COMPOSITION

[75] Inventors: Cressie E. Holcombe, Jr., Oak Ridge; Douglas D. Smith, Knoxville, both of Tenn.

[73] Assignee: The United States of America as represented by the United States Energy Research and Development Administration, Washington, D.C.

[22] Filed: Dec. 2, 1974

[21] Appl. No.: 528,765

[52] U.S. Cl. .................. 252/520; 106/39.5; 106/57; 106/73.3; 204/181; 252/518; 423/593; 423/598
[51] Int. Cl.² ............................................. H01B 1/02
[58] Field of Search ........... 106/57, 73.3, 39.5, 300, 106/299, DIG. 5; 252/518, 520; 423/593, 598

[56] References Cited
UNITED STATES PATENTS

| | | | |
|---|---|---|---|
| 2,108,544 | 2/1938 | Meyer | 106/DIG. 5 |
| 2,163,410 | 6/1939 | Pulfrich et al. | 106/DIG. 5 |
| 2,311,918 | 2/1943 | Wainer et al. | 423/598 |

FOREIGN PATENTS OR APPLICATIONS

| | | | |
|---|---|---|---|
| 924,989 | 5/1963 | United Kingdom | 106/73.3 |

OTHER PUBLICATIONS

Tien, T. Y. et al. "Microhardness of $TiO_2$—$Nb_2O_5$ Solid Solutions"—J. Am. Ceramic Soc. 52 (1969) p. 520.
Johnson, G. et al. "Influence of Minor Additions on Color & Electrical Properties of Rutile"—J. Am. Cer. Soc. 32 (1949) pp. 398–401.
Prokoshkin, D. A. et al. —"Process & Products of Oxidation of Niobium–Titanium Alloys"—Chem. Abstracts. 58 (1963). 2242A.
Trunov V. K. et al. "Double Oxides in the System $ZrO_2$—$Nb_2O_5$" Chem. Abstracts, 64 (1966) 2987C.
Durrant, P. J. et al.—Introduction to Advanced Inorganic Chemistry John Wiley & Sons N.Y. (1962) p. 977.
Durrant, P. J. et al.—Introduction to Advanced Inorganic Chemistry John Wiley & Sons N.Y. (1970) pp. 1007 & 1009.
Handbook of Chemistry & Physics (50th Ed) (1969) Pub. by Chemical Rubber Co., Cleveland, Ohio p. B134.
Ryshkewitch, E.—Oxide Ceramics—Pub. by Academic Press (1960) p. 381.
Kirk–Othmer—Encyclopedia of Chemical Technology–Vol. 22, p. 653 (1963).

*Primary Examiner*—Helen M. McCarthy
*Attorney, Agent, or Firm*—Dean E. Carlson; David S. Zachry; John B. Hardaway

[57] ABSTRACT

Oxide compositions containing niobium pentoxide and an oxide selected from the group consisting of hafnia, titania, and zirconia have electrical conductivity characteristics which vary greatly depending on the oxygen content.

4 Claims, No Drawings

3,948,813

OXYGEN SENSITIVE, REFRACTORY OXIDE COMPOSITION

BACKGROUND OF THE INVENTION

This invention was made in the course of, or under, a contract with the U.S. Atomic Energy Commission. It relates generally to the art of ceramic oxides and more particularly to the art of ceramic oxide compositions having variable electrical conductivities.

In the prior art, various methods of forming ceramic to metal seals have been utilized. Such techniques normally utilize several layers or coatings each adhering to the other until the ultimate metal and ceramic are joined into a single body. Considerations used in determining the various coatings are adhesion of one layer to the other and compatability of thermal expansion coefficients. Techniques utilized in forming such seals include the deposition of metal suspensions or metal containing compounds such as carbonyls, acetylacetonates, or nitrates onto ceramic substrates. The bond is formed by sintering in vacuum or inert gas atmospheres. The oxygen content and control of the atmosphere during sintering are important to the resulting bond strength. Another method involves sintering an oxide layer on the ceramic surface with subsequent reduction of the surface layer to metal (copper, cobalt, nickel, iron, silver, molybdenum). Noble metals are deposited on ceramics by the deposition of oil soluble noble metals compounds onto ceramic surfaces, followed by thermal decomposition of the solvent. Active metals or hydrides of zirconium, titanium, tantalum, and niobium and silver-copper eutectics are reactively sintered, after being painted onto ceramics and brought in contact with the metal. Molybdenum-manganese mixtures are layered onto ceramic substrates followed by a flash of nickel or copper and followed by heat treatment. The latter is the most widely used technique but requires three heat treatments and is sensitive to small variations in furnace atmosphere and temperatures.

An important area utilizing ceramic to metal seals is in the production of capacitors. One technique of forming a capacitor is to coat a metal film with a noble metal and to then oxidize the metal leaving the noble metal as an electrode and the metal oxide as the dielectric. This process is relatively complex and great care is required in the step of oxidation.

SUMMARY OF THE INVENTION

It is thus an object of this invention to provide a novel ceramic material which can be bonded directly to metal without the necessity of intermediate bonding layers.

It is a further object of this invention to provide a ceramic material which has electrical conductivity characteristics approximating those of a metallic conductor such that the ceramic material may be coated by conventional electrodeposition.

It is a still further object of this invention to provide a ceramic material which has a variable electrical conductivity depending upon the atmosphere in which it is heated.

These as well as other objects are accomplished by a novel ceramic material comprising niobium pentoxide and a Group IVB oxide.

DETAILED DESCRIPTION

According to this invention, it has been found that sintered compositions of $Nb_2O_5$ and Group IVB oxides exhibit wide variations in electrical conductivities based upon the prior atmosphere used in heat treatment. While oxides are generally expected to exhibit variations in electrical conductivities based upon oxygen content, the compositions of this invention exhibit room temperature electrical conductivity variations which are much greater than would be expected from conventional defect chemistry theories. The compositions of this invention can exhibit conductivities at room temperature from 0.2 mho/cm (an electrical conductor) to about $10^{-9}$ mho/cm (an insulator).

The compositions within the scope of this invention comprise $Nb_2O_5$ with an addition of a Group IVB oxide in an amount sufficient to impart an electrical resistivity of less than about $10^3$ ohm-cm when fired in a reducing atmosphere for a period of time to produce a compact which is gray to black in color. The compositions within this range include various phase relationships. Binary compounds, both congruently and incongruently melting, and solid solutions are present within the range of compositions of this invention. While not wishing to be bound by such, it is felt that the binary compounds are responsible for the remarkable variations in conductivity properties of the compositions within the scope of this invention. Such binary compounds are present within the range of from about 10 to about 90 mole % Group IVB oxide. The binary compounds are believed to be responsible for the conductivity phenomenon since the end components do not exhibit this type of behavior. Additionally, no gross changes in oxidation states have been observed to account for the conductivity phenomenon.

The compositions within the scope of this invention are preferably prepared by coprecipitating the metallic hydroxides from the ethylates, isopropylates, or tert-amylates formed by the reaction of metal chlorides with alcohols producing esterification followed by hydrolysis to form the finely mixed hydroxide precipitates. The resulting hydroxides are then converted to the oxide by calcining the vacuum-dried product at about 800°–1000°C for about 40 hours. Ceramic bodies from these compositions may be fabricated by conventional isostatic or unidirectional pressing followed by sintering at generally 80% of the absolute melting point of each particular composition. By firing the ceramic bodies in a reducing or inert atmosphere having an oxygen content of about 5–100 ppm for 2–5 hours, the room temperature electrical resistivity becomes less than about $10^3$ ohm-cm; whereas, if the bodies are fired or refired in air to about 500°–1000°C for about 4–20 hours the resistivity increases to greater than about $10^7$ ohm-cm. Accompanying the change in resistivity is also a change in color. The conducting material is gray to black in color, while the non-conducting material is substantially white.

While greater uniformity is achieved by the coprecipitation technique, the compositions may be formed by simply mixing the oxide powders, compacting and sintering by conventional techniques. In general, a temperature of about 60–80% of the respective melting point for 2–5 hours is required to approach equilibrium for sintering.

The utility of such a material is readily apparent. The conducting material may be bonded to metal by conventional electrodeposition processes. Depending upon the ultimate use intended, the material may be refired in air after electrodeposition to convert the coated material to an insulator. In the event that a capacitor is being fabricated, the coating may be machined away in the areas where no coating is desired, to leave only the portion of the metal which is to be used as an electrode. Conventional masking techniques may also be used for areas where no coating is desired.

The compositions of this invention may also be used as an intermediate in producing ceramic to metal seals between other ceramics and some metal. In such instances the composition of this invention is bonded to the particular base ceramic by coating the base ceramic with particles of these compositions (by painting or spraying a suspension of the particles followed by annealing to form a diffusion bond; by plasma or flame spraying) and then the composition is metallized as above described.

While the electrical properties of the compositions of this invention have been referred to above, the physical and mechanical properties of these materials are also excellent. Melting points range from 1405° to 1880°C. Thermal expansion coefficients are lower than most common ceramic materials ranging from 1.0 to 3.2 × $10^{-6}$/°C from ambient to 1000°C.

The materials within the scope of this invention appear to have good physical integrity even after repeated temperature cycling. Solid solutions of $TiO_2$—$Nb_2O_5$ have microhardness values of about 800 kg/mm$^2$. The modulus of rupture for $ZrO_2.3Nb_2O_5$ and $Nb_2O_5.TiO_2$ is reported to be 8.9 and 4.2 × $10^3$ psi respectively (Battelle Memorial Institute Report No. BMI-792, December 1952). The modulus of elasticity is reported to be about 9 × $10^6$ psi and 6 × $10^6$ psi for the above respective compositions at room temperature.

While the binary compounds, which are believed to be responsible for the unusual electrical properties of the compositions of this invention, are present within the range of about 10 to 90 mole % Group IVB oxides, the preferred composition is within the range of 25–75% because the end components do not exhibit the magnitudes of variation in electrical properties. For example, reduced $Nb_2O_5$ has a room temperature conductivity of $10^{-4}$ to $10^{-6}$ mho/cm.

Compositions within the scope of this invention may be electroplated as readily as most metals. Electrodepositions on black $Nb_2O_5$. $TiO_2$ and $HfO_2.3Nb_2O_5$ with Au, Cu, and Ni indicates that the compositions will plate from conventional electrolytic bath. The conductivity of these substrate materials is sufficiently high that plating from conventional plating solutions presents no difficulty. Current conditions can be varied to suit the desired rate and thickness of deposition.

Masking procedures such as used for metals can be used to plate selective areas. This can also be accomplished by plating the complete part followed by chemical etching or machining the areas where plating is not desired.

The low coefficients of thermal expansion of these materials suggests that layers as thin as possible be used in order to minimize stress if the plated area would be subjected to high temperatures. For example, a 1.0 mil layer of gold on $Nb_2O_5.TiO_2$ withstands heating in air to 600°C for 1 week without deleterious effect; whereas a 20 mil layer spalls off under such conditions.

These materials are ideal for forming hermetic ceramic to metal seals. For instance, a furnace tube (100% dense) of one of these materials can be plated with Cu and joined by silver solder to a stainless steel flange which is also Cu plated at connecting points. The ceramic tube can be subjected to high temperatures during operation while the joint would be on the furnace exterior at room temperature.

From an electroplating standpoint, any metal can be electroplated onto the ceramic compositions of this invention. The ceramic materials can be left as conductors (black) or converted to insulators (white) by heating in air to 500°–1000°C for about 4 to 20 hours depending on the part thickness and temperature.

Having generally described the invention and the compositions included therein, the following specific examples are given as a further illustration thereof.

EXAMPLE I

A composition of $Nb_2O_5$ and $HfO_2$ was prepared from niobium and hafnium chloride solutions. The metal alkoxides were prepared individually by reacting the metal chlorides with isopropanol in mole ratios of 1:5 and 1:4 for the niobium and hafnium syntheses respectively. Tert-amylates of the respective metals were formed by an ester exchange between the individual metal isopropylates and tert-amyl alcohol. The metal tert-amylates were combined in quantities to yield the desired mole ratios of metal oxides for the hafnium niobate composition and refluxed in a benzene solution for 3 hours. After cooling the refluxed solution, the metal tert-amylates were hydrolyzed to yield a precipitate of mixed hydroxides. Compositions of $HfO_2.Nb_2O_5$ and $HfO_2.3Nb_2O_5$ were prepared in this manner.

The mixed hydroxide precipitate was vacuum dried at 50°C for 24 hours. After the drying operation, the powder was calcined in air at 700°C for 40 hours. The oxide powders were isostatically pressed at 30,000 psi to form pellets of right circular cylinders of 1.5 inches length and 0.5 inch diameter (nominal) which were sintered at 1400°C for 2 hours in an argon atmosphere. The argon sintering operation produced pellets having a gray-to-black color. Electrical resistivity (D.C.) data for gray-to-black pellets are listed in Table I. Resistivity measurements were made at room temperature at 10% relative humidity using calibrated carbon-in-glass resistors as standards. A Keithly Model 500 megohm meter was used in testing.

After the property data measurements were made, the pellets were heated at 700°C in air for 1 week. A weight increase of about 0.1 wt. % was caused by the reoxidation and the color of the pellets was changed to white. Physical and chemical property data for the pellets are listed in Tables II and III. These data are practically the same for the oxidized and oxygen deficient states of the pellets. The x-ray diffraction phase analysis data are given in Table IV.

TABLE I

| ELECTRICAL RESISTIVITY measurements | | |
|---|---|---|
| | Resistivity (ohm-cm) | |
| Material | White | Gray-Black |
| $TiO_2.Nb_2O_5$ | 1 × $10^7$ | 6.2 × $10^0$ |
| $ZrO_2.3Nb_2O_5$ | 3 × $10^7$ | 5. × $10^0$ |
| $ZrO_2.Nb_2O_5$ | 4 × $10^7$ | 2.9 × $10^2$ |
| $HfO_2.3Nb_2O_5$ | 4 × $10^7$ | 3. × $10^0$ |
| $HfO_2.Nb_2O_5$ | 2 × $10^8$ | 7.1 × $10^2$ |

TABLE II

DENSITY MEASUREMENTS

| Sample Identification | Porosity (%) | Bulk Density, BD (gms/cc) | Apparent Specific Gravity, ASG (gms/cc) | Theoretical Densities (BD/ASG) 100 (%) | (BD/TD) 100 (%) | Theoretical X-Ray Densities (gms/cc) |
|---|---|---|---|---|---|---|
| $TiO_2.Nb_2O_5$ | 2.2 | 4.08 | 4.17 | 98 | 94 | 4.34 |
| $ZrO_2.3Nb_2O_5$ | 31.6 | 3.19 | 4.67 | 68 | 70 | 4.48(1,2) |
| $ZrO_2.Nb_2O_5$ | 15.1 | 4.37 | 5.13 | 85 | — | — |
| $HfO_2.3Nb_2O_5$ | 34.8 | 3.31 | 5.09 | 65 | 66 | 5.04(1,2) |
| $HfO_2.Nb_2O_5$ | 37.7 | 3.92 | 6.29 | 62 | — | — |

(1) Based on [$Me_2Nb_{10}O_{29}$ + 0.083 $\beta$-$Nb_{12}O_{29}$], with the $\beta$-$Nb_{12}O_{29}$ theoretical density of 4.58 gms/cc.
(2) Theoretical density for $Hf_2Nb_{10}O_{29}$ is 5.11 gms/cc and for $Zr_2Nb_{10}O_{29}$, 4.46 gms/cc.

TABLE III

CHEMICAL ANALYSES

| Material | Observed Values | | | | | Theoretical Values | | |
|---|---|---|---|---|---|---|---|---|
| | $MeO_2$ (wt %) | $Me_2O_5$ (wt %) | $MeO_2$ (mol %) | $Me_2O_5$ (mol %) | $MeO_2$ (wt %) | $Me_2O_5$ (wt %) | $MeO_2$ (mol %) | $Me_2O_5$ (mol %) |
| $TiO_2.Nb_2O_5$ | 24.4 | 75.8 | 52.8 | 47.2 | 23.1 | 76.9 | 50.0 | 50.0 |
| $ZrO_2.3Nb_2O_5$ | 13.2 | 86.2 | 24.9 | 75.1 | 13.4 | 86.6 | 25.0 | 75.0 |
| $ZrO_2.Nb_2O_5$ | 31.6 | 65.6 | 49.8 | 50.2 | 31.7 | 68.3 | 50.0 | 50.0 |
| $HfO_2.3Nb_2O_5$ | 20.2 | 79.3 | 24.3 | 75.7 | 20.9 | 79.1 | 25.0 | 75.0 |
| $HfO_2.Nb_2O_5$ | 43.0 | 55.1 | 48.6 | 51.4 | 44.2 | 55.8 | 50.0 | 50.0 |

TABLE IV

X-RAY DIFFRACTION PHASE ANALYSIS

| Material | Major | Intermediate | Minor |
|---|---|---|---|
| $TiO_2.Nb_2O_5$ | $Nb_2TiO_7$ | — | $Nb_2O_5$ (Weak) |
| $ZrO_2.3Nb_2O_5$ | $Zr_2Nb_{10}O_{29}$ | — | $\beta$-$Nb_2O_5$ (Weak) |
| $ZrO_2.Nb_2O_5$ | $Nb_2Zr_6O_{17}$(SS) | HT-$Nb_2O_5$(SS) | — |
| $HfO_2.3Nb_2O_5$ | $Hf_2Nb_{10}O_{29}$ | — | $\beta$-$Nb_2O_5$ (Weak) |
| $HfO_2.Nb_2O_5$ | $Nb_2Hf_6O_{17}$(SS) | HT-$Nb_2O_5$(SS) | — |

SS = Solid Solution;
HT = High Temperature Modification

EXAMPLE II

A cylindrical-shaped composition of $Nb_2O_5$ and $TiO_2$ in a mole ratio of 1:1 was prepared in the manner described in Example I. The sintered cylinder had a diameter of 0.5 inch and a length of about 1.5 inch.

Physical and chemical property data are listed in Tables II and III. The electrical resistivity measurements are given in Table I and the x-ray diffraction phase data are provided in Table IV.

EXAMPLE III

A composition of $ZrO_2$ and $Nb_2O_5$ in mole ratios of 1:1 and 1:3 was prepared by the procedure described in Example I.

The physical and chemical property data for the pellets are listed in Tables II and III. The electrical resistivity measurements are given in Table I and the x-ray diffraction data are provided in Table IV.

EXAMPLE IV

A pellet of $Nb_2O_5.TiO_2$ which was 1 cm in diameter and 0.3 cm thick (cut from the previously described sintered rod with a diamond saw) was electroplated with nickel utilizing the standard nickel sulfamate bath and conditions as follows:

| Bath Constituents | Concentration |
|---|---|
| Nickel sulfamate | 45 oz/gal |
| Nickel metal content | 10 oz/gal |
| Nickel chloride | 0.1 oz/gal |
| Boric acid | 4.5 oz/gal |
| Sodium lauryl sulfate | Amount necessary to give surface tension of 35 dynes or less |

Conditions
pH: 4.0–4.5
Temp: 130°F
Current density: 10–20A/ft² (0.011A/cm² – 0.022A/cm²)
Deposition rate: 0.5–1.0 mil/hr With these conditions, a nickel coating thickness of 1.0 ± 0.1 mil was achieved using 0.05A in 1 hour. The coating appeared shiny and adherent.

EXAMPLE V

Gold was plated on $Nb_2O_5.TiO_2$ (same size pellet as in Example IV) using the following acid citrate bath:

"Temperex HD" at a concentration of 1 troy ounce of Au/gal, at a temperature of 160°F, and at a current density of 7A/ft² (0.0075A/cm²), which yields a deposition rate of 1 mil/hr.

Thus the required current density was achieved with 0.02A. Thicknesses of 1 mil and 19–20 mil respectively were applied to two samples. The plated areas around the periphery of the pellets were sanded off and the pellets were subsequently heated to 600°C for 1 week in air. The gold layer had partly released from the thicker-coated specimen after sanding the edges, and completely slaked off after heating. The 1 mil thick coated pellet, however, appeared to have good adherence after heating. Both $Nb_2O_5.TiO_2$ pellets were white in color and were insulators.

The above conditions were also used to Au plate a $HfO_2.3Nb_2O_5$ (diameter = 1.3 cm; t = 0.3 cm) with a 1 mil thickness.

EXAMPLE VI

Copper was plated onto $Nb_2O_5 \cdot TiO_2$ (pellet 1 cm diameter by 0.5 cm thick) using the following (bright) acid sulphate bath:

"Udylite" bright acid copper bath comprising
Copper sulfate — 28 oz/gal
Sulfuric acid — 7 oz/gal at room temperature and at a current density of 20A/ft$^2$ (0.022 A/cm$^2$), which yields a 1 mil/hr deposition rate.

A 0.5 mil thickness was applied to the entire surface and appeared to adhere well.

EXAMPLE VII

A slurry of $HfO_2 \cdot 3Nb_2O_5$ (white, insulating powder from crushing pellet) was prepared using a 1% ammonium alginate solution as the suspending agent. This slurry was painted on a 99.9% purity, 100% dense $Al_2O_3$, 1 inch diameter disc. After drying (50°C, 30 minutes), the disc was heated to 1200°C in argon and soaked for 1 hour. The $HfO_2$-$3Nb_2O_5$ apparently diffused into the $Al_2O_3$ forming an adherent black film. The resistance of the film across the 1 inch diameter was $5 \times 10^4$ ohms. This implied that a thicker coating would form a conductive film on $Al_2O_3$ by this technique.

While the term Group IVB oxide has been used to designate an oxide selected from the group consisting of hafnia, titania, and zirconia, no appreciable differences in the conductivity phenomenon have been found for the various oxides, and thus all are substantial equivalents of one another. Specific applications and economic considerations, however, may indicate that one oxide is to be preferred over the other.

What is claimed is:

1. A sintered compact composition consisting essentially of 25 to 75 mole % $Nb_2O_5$ with the balance being a Group IVB dioxide, said compact being gray to black in color with an electrical resistivity of less than $10^3$ ohm-cm, containing binary compounds consisting essentially of integer molar ratios of $Nb_2O_5$ and said Group IVB dioxide and being capable of direct electrodeposition of an adjacent metallic layer and of conversion to an insulator substantially white in color when heated in air.

2. The composition according to claim 1 wherein said Group IVB dioxide is $HfO_2$.

3. The composition according to claim 1 wherein said Group IVB dioxide is $TiO_2$.

4. The composition according to claim 1 wherein said Group IVB dioxide is $ZrO_2$.

* * * * *